United States Patent
Lavi

(10) Patent No.: US 11,883,074 B2
(45) Date of Patent: Jan. 30, 2024

(54) HOLE TRANSPORTER

(71) Applicant: Orthex, LLC, Banpo Bridge, FL (US)

(72) Inventor: Abraham Lavi, Banpo Bridge, FL (US)

(73) Assignee: Orthex, LLC, Warsaw, IN (US)

( * ) Notice: Subject to any disclaimer, the term of this patent is extended or adjusted under 35 U.S.C. 154(b) by 0 days.

(21) Appl. No.: 16/567,061

(22) Filed: Sep. 11, 2019

(65) Prior Publication Data
US 2020/0170675 A1    Jun. 4, 2020

Related U.S. Application Data

(60) Provisional application No. 62/728,296, filed on Sep. 7, 2018, provisional application No. 62/728,260, filed on Sep. 7, 2018.

(51) Int. Cl.
*A61B 17/62* (2006.01)
*A61B 17/64* (2006.01)

(52) U.S. Cl.
CPC .......... *A61B 17/6458* (2013.01); *A61B 17/62* (2013.01)

(58) Field of Classification Search
CPC ............................. A61B 17/60–666
See application file for complete search history.

(56) References Cited

U.S. PATENT DOCUMENTS

| | | | | |
|---|---|---|---|---|
| 4,365,624 A * | 12/1982 | Jaquet | ................ | A61B 17/6441 606/56 |
| 5,087,258 A * | 2/1992 | Schewior | ............... | A61B 17/62 606/56 |
| 5,443,464 A * | 8/1995 | Russell | ............... | A61B 17/6483 606/54 |
| 5,487,741 A * | 1/1996 | Maruyama | ......... | A61B 17/8085 606/71 |
| 5,496,319 A * | 3/1996 | Allard | ................ | A61B 17/6441 403/4 |
| 5,797,908 A * | 8/1998 | Meyers | ............... | A61B 17/6483 606/54 |
| 5,863,292 A * | 1/1999 | Tosic | ..................... | A61B 17/66 606/56 |
| 5,885,282 A * | 3/1999 | Szabo | .................... | A61B 17/62 606/56 |
| 7,367,977 B2 * | 5/2008 | Estrada, Jr. | ........ | A61B 17/6416 606/53 |
| 7,422,593 B2 * | 9/2008 | Cresina | .................. | A61B 17/66 606/54 |
| 9,101,398 B2 * | 8/2015 | Singh | ..................... | A61B 17/66 |
| 10,874,433 B2 * | 12/2020 | Mannanal | ............... | A61B 17/62 |
| 2013/0172888 A1 * | 7/2013 | Necuze | .................. | A61B 17/66 606/59 |
| 2015/0238229 A1 * | 8/2015 | Khanna | ................ | A61B 17/688 606/70 |
| 2017/0354439 A1 * | 12/2017 | Mannanal | ............... | A61B 17/62 |

* cited by examiner

*Primary Examiner* — Lynnsy M Summitt
(74) *Attorney, Agent, or Firm* — Gerald W. Roberts; John V. Daniluck; Dentons Bingham Greenebaum LLP

(57) ABSTRACT

The present invention is a hole extender, in which a hole transporter includes a transport beam having a first flange with a first flange pin and a first flange hole, and at the other end of the transport beam is a second flange with a second flange hole. Key features of the present hole transporter include that the main direction of each flange is perpendicular to the beam, and the direction of the second flange hole is parallel to the direction of the first flange hole.

5 Claims, 4 Drawing Sheets

HOLE TRANSPORTER

This patent application claims priority to, and incorporates herein by reference, U.S. provisional patent application No. 62/728,260 filed 7 Sep. 2018 and U.S. provisional patent application No. 62/728,296, filed 7 Sep. 2018.

FIELD OF THE INVENTION

The present hole transporter is an accessory for use with external fixators, and specifically is for use with external fixator rings having two rings of holes therein—a standard construction for external fixator rings at this writing.

BACKGROUND OF THE INVENTION

Background of the Invention: As surgical and fixator correction of orthopedic conditions becomes more sophisticated, the hardware, software and know-how in the external fixator profession has to evolve to keep up. In particular, in external fixation applications in which specialized or extended angles of fixation must be implemented, sometimes the traditional two-ring arrangement is not quite versatile enough—for example, when a surgeon wants to affix a traditional strut to a hole in the ring, but the strut cannot reach the ring given the geometric reality involved. In a situation such as this, the surgeon needs a "hole transporter," that is, a way to extend and reposition the erstwhile hole in the ring to an extended location that retains the same orthogonal orientation as born by the hole actually present on the ring.

SUMMARY OF THE INVENTION

In order to meet this need, the present invention is a hole extender, in which a hole transporter includes a transport beam having a first flange with a first flange pin and a first flange hole, and at the other end of the transport beam is a second flange with a second flange hole. Key features of the present hole transporter include that the main direction of each flange is perpendicular to the beam, and the direction of the second flange hole is parallel to the direction of the first flange hole. With this construction and orientation, a hole present in an external fixator ring can be recreated, in a position extended away from the ring, with the new hole's being parallel to the analogous ring hole position, and with no angular distortion's having been introduced by keeping the holes parallel.

DETAILED DESCRIPTION OF THE INVENTION

The nonobviousness of the present hole transporter does not mean that the present device is structurally complicated.

Figure 1:
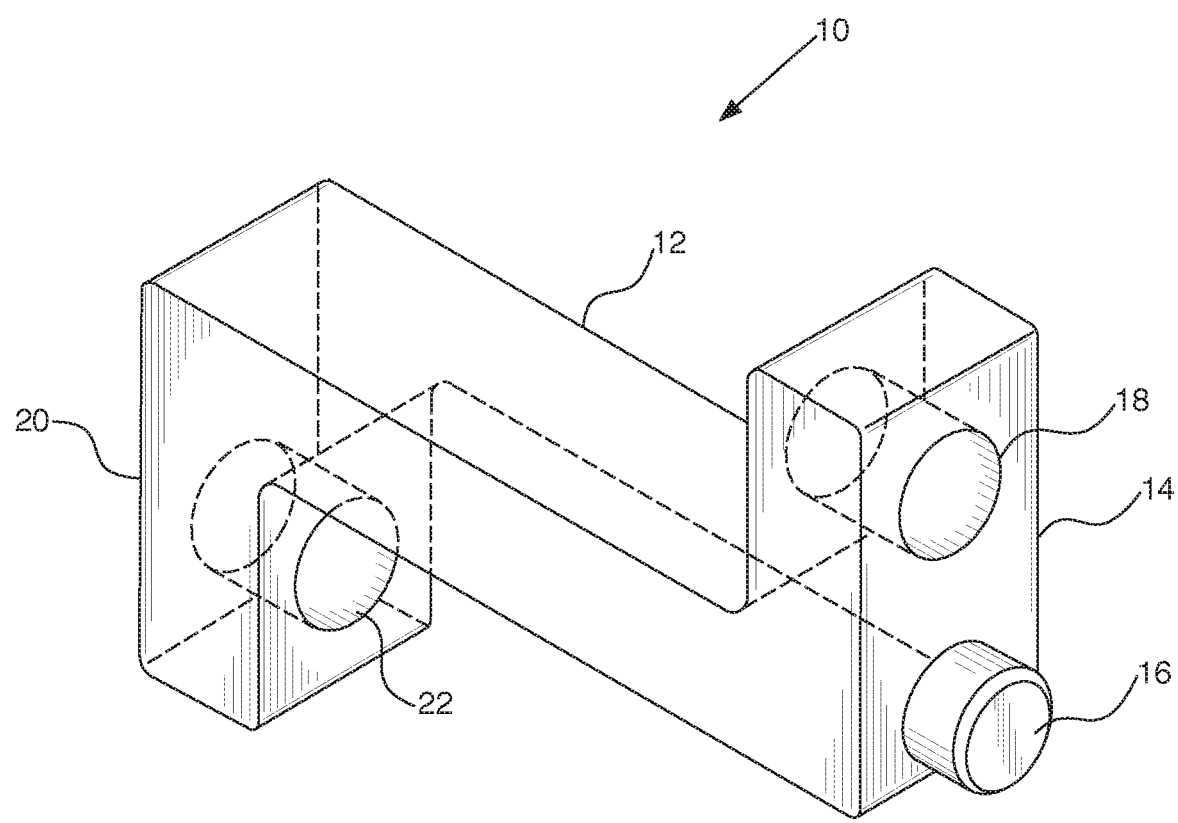
FIG. 1 is a perspective view of a hole transporter according to the present invention.

Referring now to FIG. 1, the hole transporter 10 bears a central structure, namely, a transport beam 12. At either end of the transport beam 12 are flanges 14 and 20. More particularly, first flange 14 bears first flange pin 16 and first flange hole 18, whereas second flange 20 bears second flange hole 22. In operation, the first flange pin 16 is placed in any hole of a two-ring-of-holes external fixator ring (see analogous FIGS. 4A and 4B) and the first flange hole 18 is used to bolt the hole transporter 10 to that ring. Upon securing the hole transporter to an external fixator ring, the surgeon now has access to the second flange hole 22 in an extended location relative to the ring, allowing the surgeon to secure a strut to the second flange hole 22 when he or she cannot reach the original holes in the ring with the strut.

Figure 2:
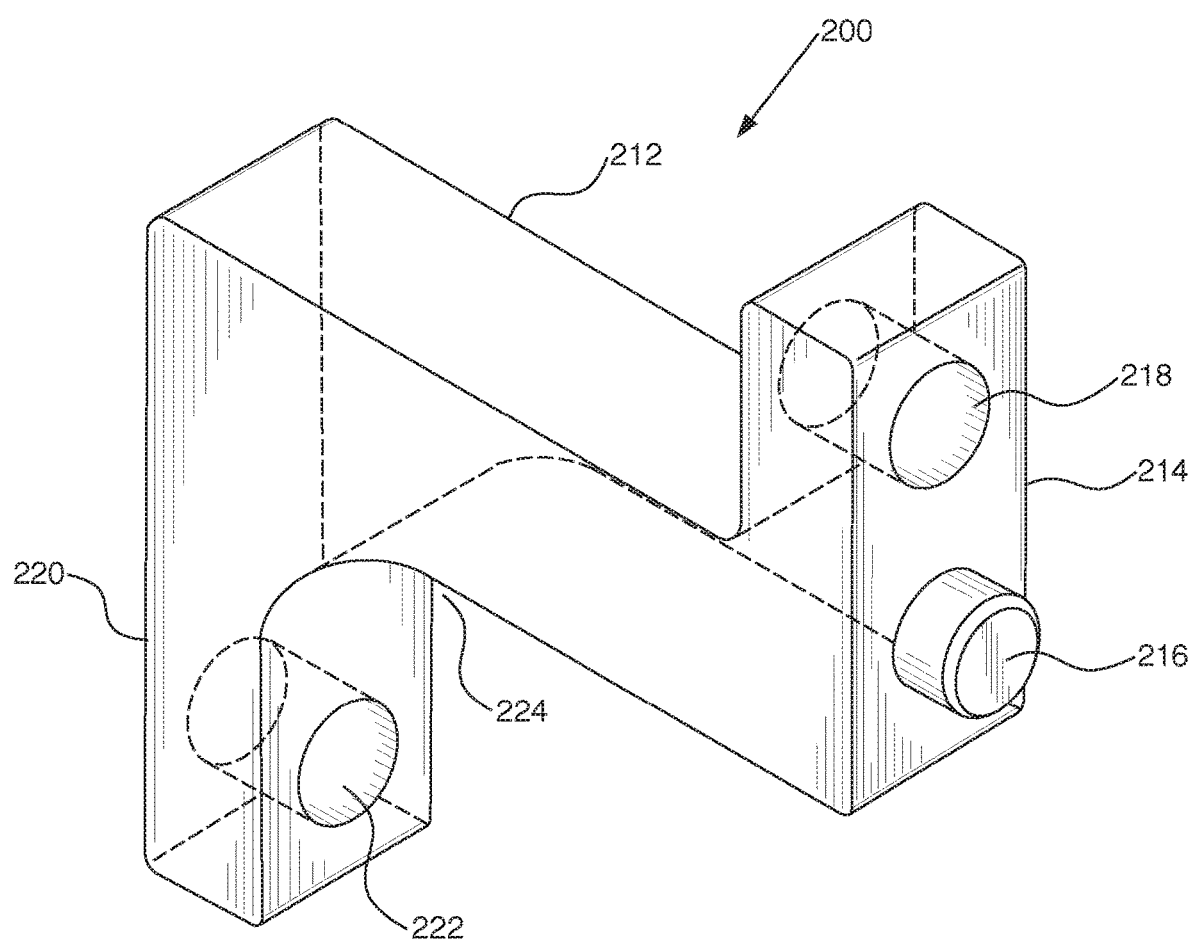
FIG. 2 is a perspective view of a second embodiment of the invention.

Referring now to FIG. 2, the hole transporter 200 bears a central structure, namely, a transport beam 212. At either end of the transport beam 212 are flanges 214 and 220. More particularly, first flange 214 bears first flange pin 216 and first flange hole 218, whereas second flange 220 bears second flange hole 222. In operation, the first flange pin 216 is placed in any hole of a two-ring-of-holes external fixator ring and the first flange hole 218 is used to bolt the hole transporter 210 to that ring. Upon securing the hole transporter to an external fixator ring, the surgeon now has access to the second flange hole 222 in an extended location relative to the ring, allowing the surgeon to secure a strut to the second flange hole 222 when he or she cannot reach the original holes in the ring with the strut. The difference between the transport beam 12 of FIG. 1 and the transport beam 212 of FIG. 2 is that the transport beam 12 of FIG. 1 is spaced geometrically closer in horizontal distance to the second flange hole 22 whereas there is a greater distance, shown in FIG. 2, from the second flange hole 222 to the transport beam 212, which transport beam 212 is also arched on its lower face with a curved surface 224 instead of a rectangular one.

Figure 3:
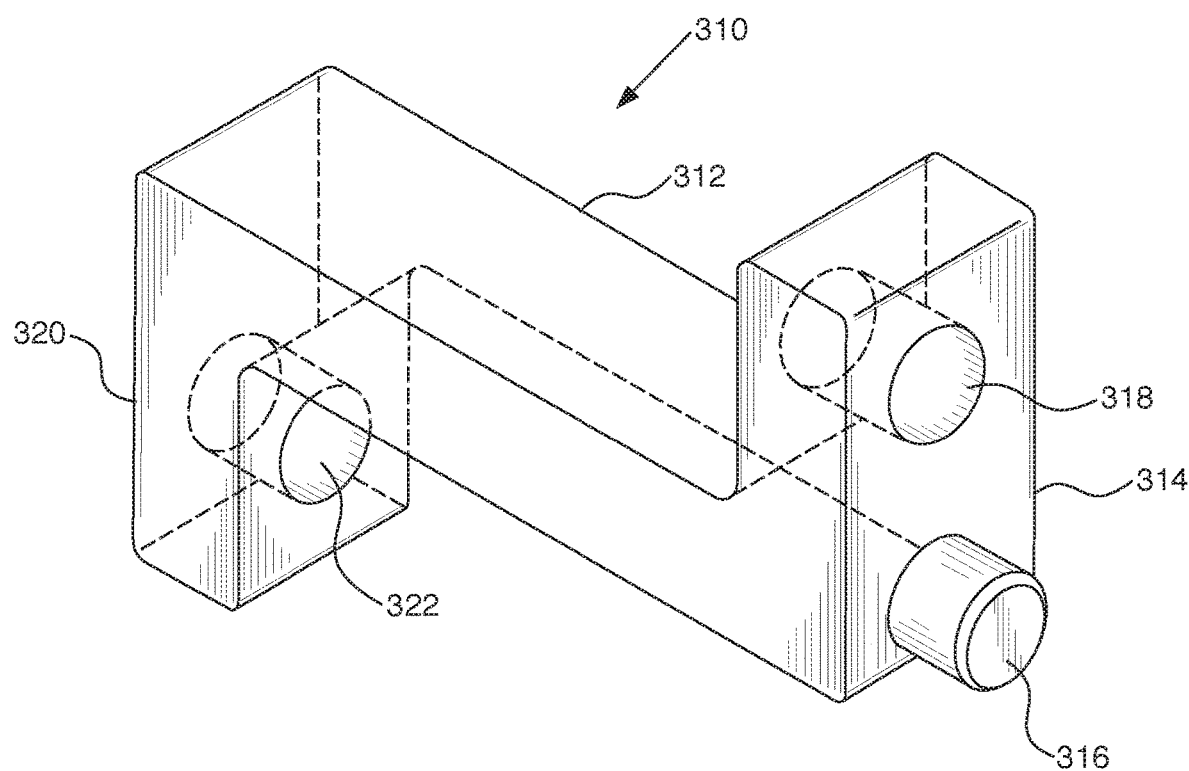
FIG. 3 is a perspective view of a third embodiment of the invention.

Referring now to FIG. 3, the hole transporter 310 is largely similar to the hole transporter of FIG. 1, but represents that gauges and dimensions can be slightly different or different as long as the general shape remains the same. For example, the first flange pin 316 of FIG. 3 has a greater length than the first flange pin of FIG. 1. In certain circumstances the surgeon or technician may want the additional stability afforded by a longer first flange pin, as a matter of judgment.

Figure 4A:
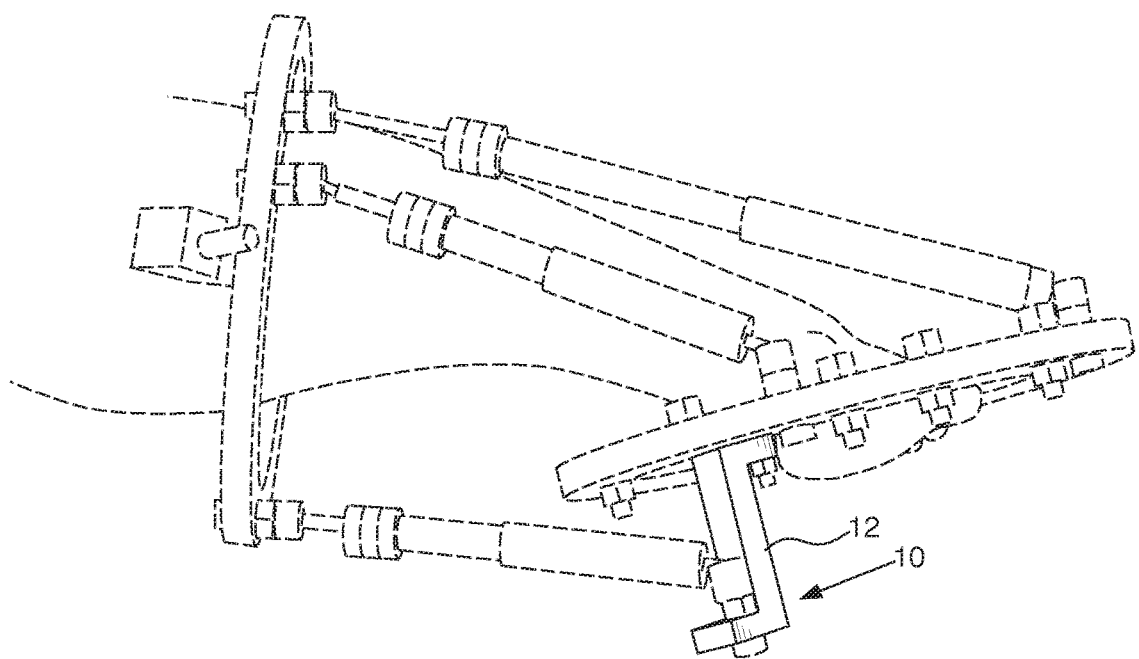
FIGS. 4A and 4B are perspective views of the present hole transporter shown in context, with the patient's limb to be treated, and associated external fixator hardware with which the hole transporter cooperates, being shown in dotted lines.
Figure 4B:
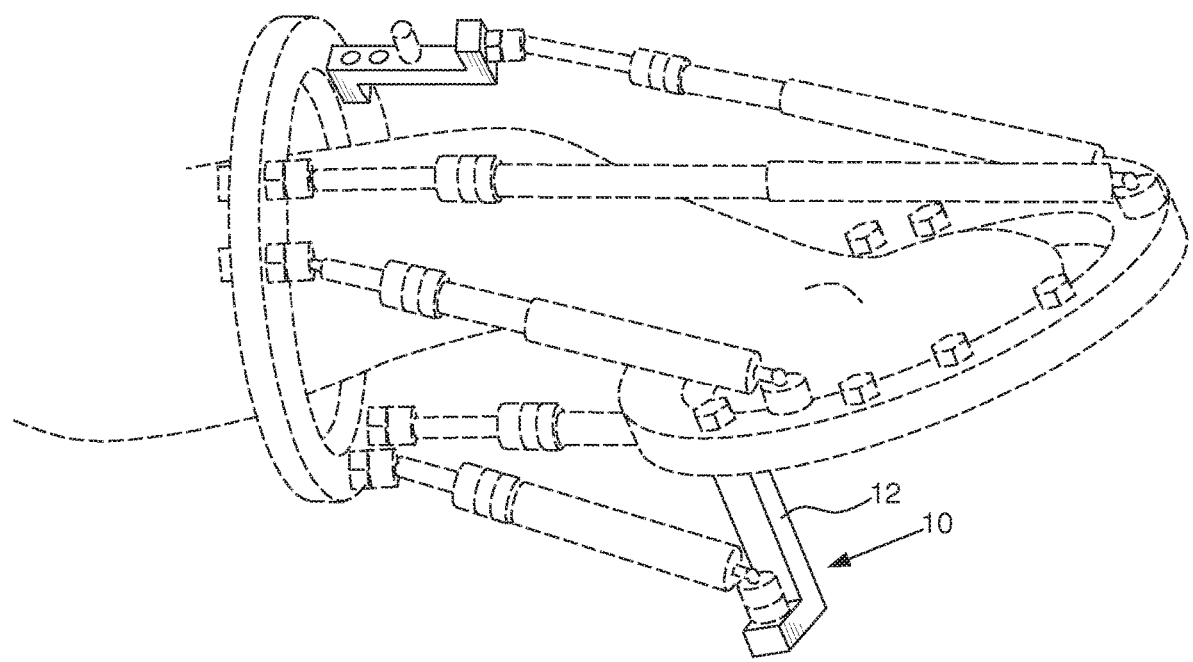

The ability of the hole transporter to provide an effective relocation of a hole to an extended location is more easily seen in FIGS. 4A and 4B. Referring now to FIG. 4A, the lowermost strut can be seen to be attached to its adjacent ring via a present hole transporter 10 (see FIG. 1) which effectually moves the anchor hole from the ring (so to speak) to a parallel position on the hole transporter. A similar arrangement is apparent in FIG. 4B, shown from a different angle. A pediatric patient's foot is shown in dotted lines, as are the ring and struts with which the present hole transporter cooperates.

A key feature of all versions of the hole transporter is that the flanges are all at right angles to the transport beam. This is true even if for design, comfort or construction reasons, a surface of a flange may be curved—the predominant angle of each flange is normal to the transport beam that bears it.

Minor variations in dimensions or flange surface curve do not change the essence of the invention described above. The point, in all the embodiments of the invention, is to provide a fixator accessory that makes it possible to extend or relocate—or transport—a hole on the fixator ring to an adjacent or extended location—without throwing off the angles of fixation.

The device would work the same if the first flange had two holes, instead of a hole and a pin. This is because an additional pin, peg or connector could be added to substitute for the pin shown in the drawings. The device can also be used with external fixator rings even if those ring are not fitted with two concentric rings of holes—because the hole transporter can be affixed to any two adjacent holes, they do not necessarily need to be holes from adjacent rings of holes. Having said that, a preferred embodiment is to affix the present hole transporter to two holes that are adjacent holes wherein each hole is part of a separate concentric ring of holes on said external fixator ring. The hole transporter may be made of steel, titanium and its alloys, or any other structural material suitable for use in external fixator ring array deployments.

Although the invention has been described with particularity above, the invention is only to be limited insofar as is set forth in the accompanying claims.

I claim:

1. A hole transporter, comprising:
   a longitudinally extending central transport beam;
   a first flange at a first end of said longitudinally extending central transport beam; and
   a second flange at a second end of said longitudinally extending central transport beam,
   wherein said flanges are at right angles to said longitudinally extending central transport beam,
   wherein a portion of said first flange extends radially from said longitudinally extending central transport beam, bears a first flange pin having a longitudinal axis, and defines a first flange hole displaced from said first flange pin,
   wherein a portion of said second flange extends radially from said longitudinally extending central transport beam and defines a second flange hole,
   wherein said radial extension of said portion of said first flange, said longitudinal extension of said central transport beam, and said radial extension of said portion of said second flange conform to a generally Z-shaped geometry,
   wherein said longitudinal axis of said first flange pin extends through said longitudinally extending central transport beam, and
   wherein said first flange pin has a first overall length, said first flange hole has a second overall length, and said first overall length is approximately half as great as said second overall length.

2. An apparatus, comprising:
   a longitudinally extending central transport beam;
   a first flange at a first end of said longitudinally extending central transport beam;
   a second flange at a second end of said longitudinally extending central transport beam; and
   an external fixator ring defining an in-external-fixator-ring hole,
   wherein said flanges are at right angles to said longitudinally extending central transport beam,
   wherein a portion of said first flange extends radially from said longitudinally extending central transport beam, bears a first flange pin having a longitudinal axis, and defines a first flange hole displaced from said first flange pin,
   wherein a portion of said second flange extends radially from said longitudinally extending central transport beam and defines a second flange hole,
   wherein said radial extension of said portion of said first flange, said longitudinal extension of said central transport beam, and said radial extension of said portion of said second flange conform to a generally Z-shaped geometry,
   wherein said longitudinal axis of said first flange pin extends through said longitudinally extending central transport beam,
   wherein said in-external-fixator-ring hole receives said first flange pin therein, and
   wherein said external fixator ring bolts to said first flange via said first flange hole.

3. The apparatus of claim 2, wherein said longitudinally extending central transport beam and said flanges are respective portions of a unitary article.

4. The apparatus of claim 2, further comprising an external fixator strut secured to said second flange hole.

5. The apparatus of claim 4, wherein said longitudinally extending central transport beam and said flanges are respective portions of a unitary article.

* * * * *